United States Patent
Salem

(10) Patent No.: US 9,747,417 B2
(45) Date of Patent: Aug. 29, 2017

(54) METHOD AND APPARATUS FOR ENHANCED PERSONAL CARE

(71) Applicant: Mores, Inc., Burbank, CA (US)

(72) Inventor: Ayman Salem, Los Angeles, CA (US)

(73) Assignee: Mores, Inc., Burbank, CA (US)

( * ) Notice: Subject to any disclaimer, the term of this patent is extended or adjusted under 35 U.S.C. 154(b) by 0 days.

(21) Appl. No.: 14/080,021

(22) Filed: Nov. 14, 2013

(65) Prior Publication Data

US 2015/0134773 A1     May 14, 2015

(51) Int. Cl.
    *G06F 19/00*      (2011.01)

(52) U.S. Cl.
    CPC ...... *G06F 19/3418* (2013.01); *G06F 19/3456* (2013.01); *G06F 19/3462* (2013.01); *G06F 19/3475* (2013.01); *G06F 19/3481* (2013.01)

(58) Field of Classification Search
    CPC   H04L 29/08072; H04L 29/06; H04L 29/0809
See application file for complete search history.

(56) References Cited

U.S. PATENT DOCUMENTS

| | | | |
|---|---|---|---|
| 2007/0159316 A1* | 7/2007 | Mischel, Jr. | A47G 1/02 340/461 |
| 2008/0004748 A1* | 1/2008 | Butler | G06Q 30/02 700/244 |
| 2008/0058615 A1* | 3/2008 | Clapp | G06F 19/327 600/301 |
| 2011/0054936 A1* | 3/2011 | Cowan | G06F 19/322 705/3 |
| 2012/0151697 A1 | 6/2012 | Farrell et al. | |
| 2014/0173269 A1* | 6/2014 | Varoglu | H04L 51/18 713/150 |

FOREIGN PATENT DOCUMENTS

WO    WO 2013/102398     7/2013

* cited by examiner

*Primary Examiner* — Vivek Srivastava
*Assistant Examiner* — Hien Doan
(74) *Attorney, Agent, or Firm* — Smyrski Law Group, A P.C.

(57) ABSTRACT

A method and apparatus for enhancing a user's lifestyle and personal care is provided. The design includes a device having a display/mirror and a plurality of connection ports each configured to receive a personal care module configured to facilitate the personal care of a user and a remote device arrangement. The device is configured to provide user personal care communications to and receive user personal care communications from the remote device arrangement, and wherein the device is configured for the user to freely substitute personal care modules.

17 Claims, 13 Drawing Sheets

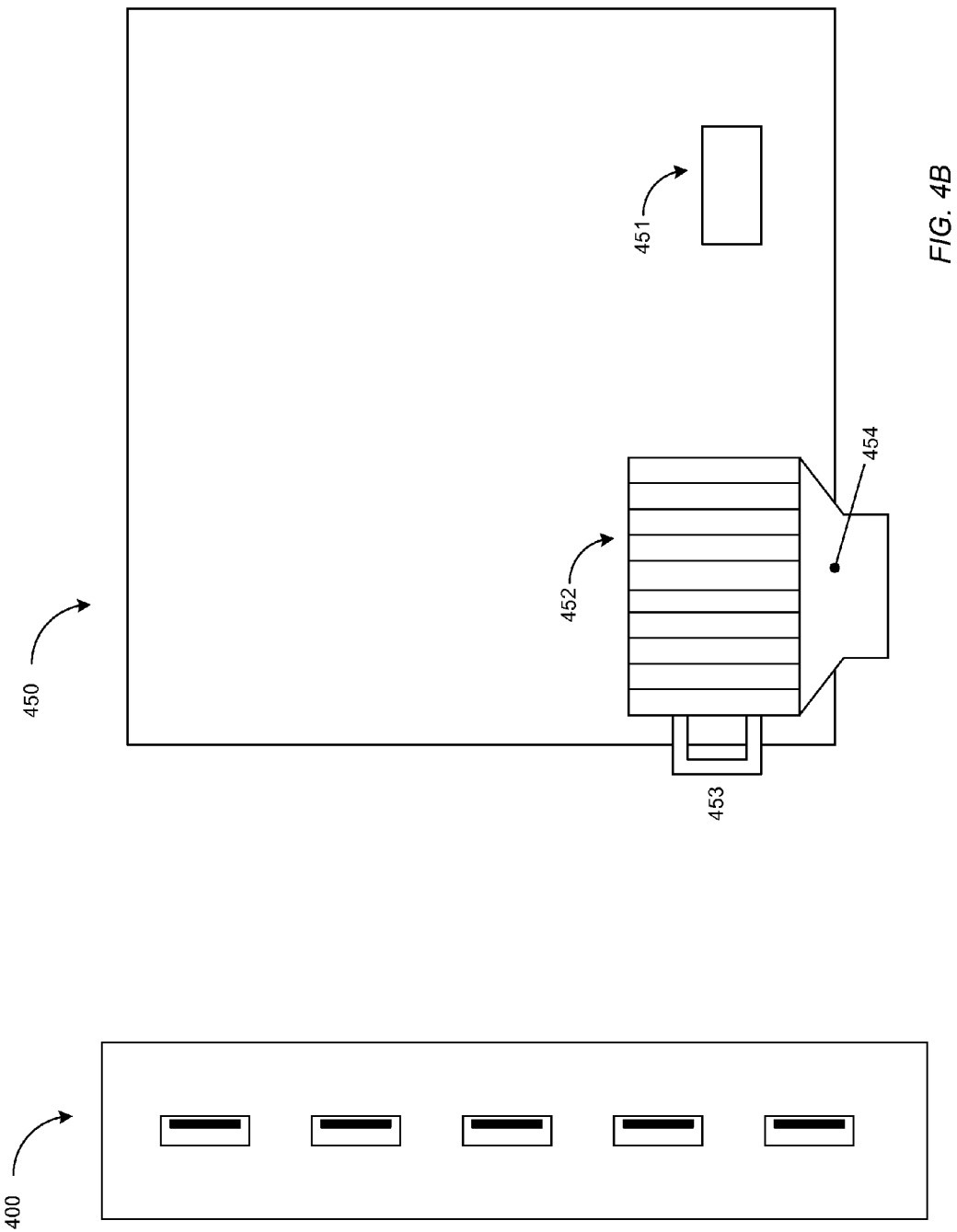

METHOD AND APPARATUS FOR ENHANCED PERSONAL CARE

BACKGROUND OF THE INVENTION

Field of the Invention

The present invention relates in general to personal care, and more specifically enabling a user to monitor, assess, maintain and receive information to improve personal care and lifestyle attributes, including but not limited to user health, physical appearance, fashion, fitness, cosmetics and wellness.

Description of the Related Art

People seek to improve or at least maintain their personal care on a daily basis. Whether monitoring their own personal health, appearance, fitness, or wellness, for example, people purchase and use an array of products and services. In the area of health care and maintenance alone, people may be taking a series of medications, may need to be monitored on a regular basis for a condition, may have an injury that needs to be evaluated for progress, and so forth. Each of these wellness tasks requires a different product or service. An individual may need to make a trip to a physician, then to a pharmacist to obtain a prescription, may need to purchase over-the-counter health care products, and may require a long term care giver to provide necessary personal care. At a later time, the individual may need to obtain further products or services—sometimes as frequently as on a daily basis.

Other areas of personal care, such as cosmetics, wardrobe and so forth, also require a series of products and/or services, and in some instances recommendations or decisions, to carry out and achieve a desired level of personal care. People have previously needed to locate and then obtain all necessary personal care products and services from a myriad of sources, typically requiring traveling to multiple locations, making purchases from several web sites, and/or generally spending a great deal of time and effort to maintain their personal appearance and well-being. In some instances, the desired product or service can be difficult or impossible to obtain due to mass production constraints or other. Therefore industry products are not personalized as such.

It would be highly beneficial if multiple aspects of personal care could be obtained from a readily accessible system or device, where such a system could provide personalized care directed to the specific needs or desires of an individual user.

SUMMARY OF THE INVENTION

According to one aspect of the present design, there is provided a device having a display/mirror and a plurality of connection ports each configured to receive a personal care module configured to facilitate the personal care of a user and a remote device arrangement. The device is configured to provide user personal care communications to and receive user personal care communications from the remote device arrangement, and wherein the device is configured for the user to freely substitute personal care modules.

According to another embodiment, there is provided a method for facilitating personal care of a user. The method includes receiving, at a remote device arrangement, user personal care data transmitted by a user personal care computing device, determining at the remote device arrangement a user personal care recommendation specific for the user based on the user personal care data received, and transmitting the user personal care recommendation to the user personal care computing device.

According to another embodiment, there is provided a personal care device, comprising a computing device display that is a mirror, and a housing surrounding the computing device display that operates as the mirror, the housing comprising a plurality of connection ports configured to receive personal care modules configured to facilitate personal care of a user. The housing comprises one from a group consisting of a camera, a microphone, a speaker, a sensor, and a fingerprint reader.

These and other advantages of the present invention will become apparent to those skilled in the art from the following detailed description of the invention and the accompanying drawings.

BRIEF DESCRIPTION OF THE DRAWINGS

For a more complete understanding of the present disclosure, reference is now made to the following figures, wherein like reference numbers refer to similar items throughout the figures:

FIG. 4A illustrates a side view of a device similar to that shown in FIG. 2;

FIG. 4B is a rear view of an embodiment of the device;

The exemplification set out herein illustrates particular embodiments, and such exemplification is not intended to be construed as limiting in any manner.

DETAILED DESCRIPTION OF THE INVENTION

The following description and the drawings illustrate specific embodiments sufficiently to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

In general, the present invention includes personal care system that employs modular hardware configured to offer personal care information, products, and services directed to a specific user. The present design may take the form of a device including a mirror having processing and communication capability and configured with a plurality of connection points, the connection points allowing personal care modules to be connected to the device. Additional functionality may be provided with the mirror in a central or main hardware component. In this manner, an individual can maintain a device at her residence or place of work or elsewhere that can be configured to meet her personal care needs.

The system may include a portable device configured to be taken with the user, while traveling locally or long distance, and connect with the base device such that the user may record desired information and provide the information to the base location at a later time.

Additionally, the present system may include a communications network, which may be server or cloud based, wherein the user can store personal care information, obtain personal care information such as recommendations specific to the user, may schedule and receive reminders, and so forth.

Figure 1:
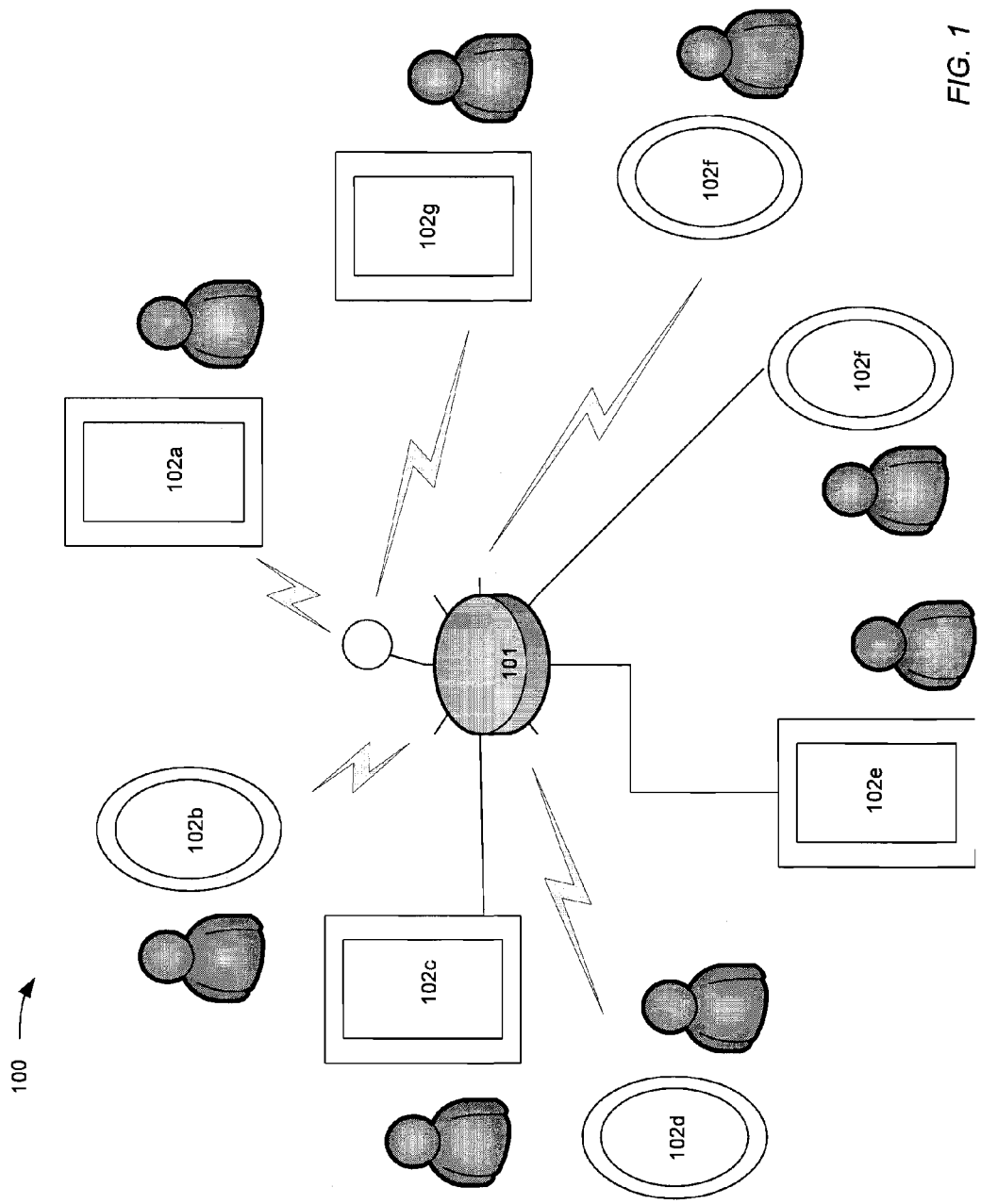
FIG. 1 is a general system overview of the present design.

FIG. 1 is a general system overview of the present design. From FIG. 1, network 100 includes a processing and storage site 101, also referred to as a remote device arrangement herein, configured to communicate with and receive communications from personal care devices 102a-h. Communication may be effectuated between the processing and storage site 101 and the personal care devices 102a-h in any manner known and available, including but not limited to interne connectivity via wire, wireless (802.11a/b/n/g, Wi fi), cellular, and or other communication means. While a single processing and storage site 101 is shown, it is to be understood that more than one such site may be employed and more than one such site may carry out some of the functionality disclosed herein.

In general, information about an individual's personal care may be obtained at a personal care device, e.g. personal care device 102b, and this information may be communicated to processing and storage site 101. Information about personal care generally falls into five categories, but other categories may be employed or provided, the five categories including health, fitness/wellness, fashion, cosmetics, and pharmaceuticals. While personal care device 102b may offer such capabilities, a user may or may not employ all capabilities. A user may simply wish to employ the present design for health purposes. Information obtained may be manually entered by the user or obtained using a set of readings or information obtained at the device, and/or information may be provided to the personal care device 102b from the processing and storage site. As an example, blood pressure readings may be made by the user using the personal care device, the blood pressure information may be provided from the personal care device 102b to the processing and storage site 101, and the processing and storage site 101 may provide a recommendation back to the user, even something as innocuous as "You have a slightly elevated blood pressure. The following may be potential meal suggestions for the coming days." As may be understood, any type of interaction between the user, user device 102b, and processing and storage site 101 may be employed as desirable, such as determining the user's body type and recommending clothing for the user, determining skin tone and making a recommendation for particular skin care and/or cosmetic purchases, and so forth.

Figure 2A:
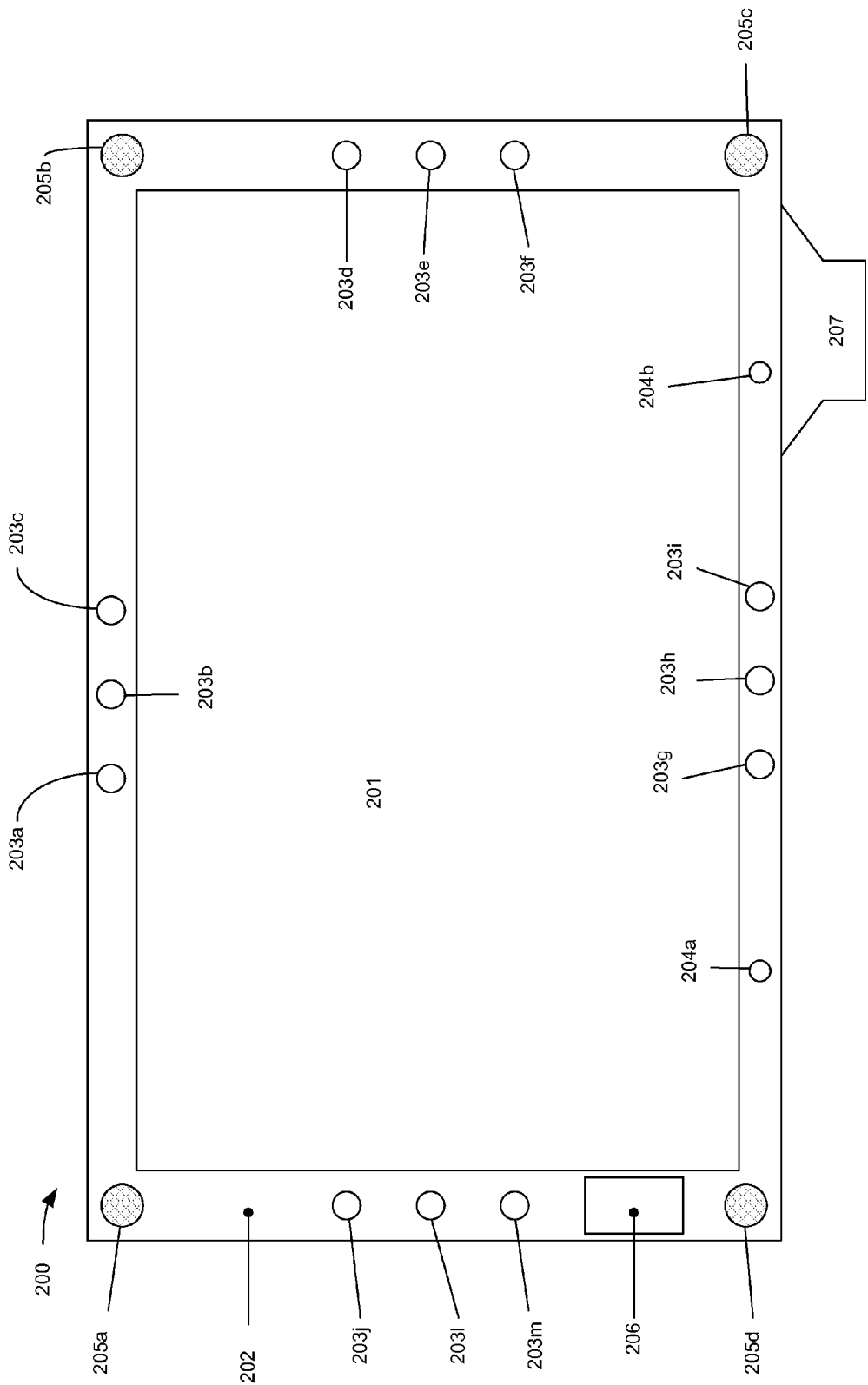
FIG. 2A illustrates a rectangular embodiment of one aspect of the present design.

One embodiment of the present design is presented in FIG. 2A. The device 200 includes a central element 201, typically a mirror that operates as a display screen as well. Such devices are available from, for example, Ox-Home (ox-home.com) or Samsung, with the Samsung product called the LED mirror TV. Edge element 202 may be provided and made from any suitable material, and shown in FIG. 2A are cameras 203a-1, microphones 204a and 204b, speakers 205a-d, and sensor, voice, or fingerprint reader 206. The sensor may be any type of sensor (biometric, heat, or otherwise), and a voice recognition component may be present, operating separately or using microphones 204a and 204b together with voice recognition software. Also shown in this view is an optional pill dispenser tray 207. While a certain number of components are shown in FIG. 2A, it is to be understood that any number of components may be employed and the invention is not so limited.

The user may stand in front of device 200 and view her reflection. She may verify her identity using fingerprint reader 206, where fingerprint reader 206 may connect to a processor as discussed below and may be able to verify a user's identity. Device 200 may photograph or visually record the user using one or more of cameras 203a-1. The user may speak words that may be received by microphones 204a and 204b, and the device 200 may speak words or provide audio information using speakers 205a-d.

Not shown in FIG. 2A is a series of connection slots in the device, typically in the FIG. 2A embodiment positioned on the outer edges of the device. The connection slots enable the user to connect modules having specialized functionality to the device for the purpose of facilitating personal care. A user can plug one or more modules into the device and can obtain desired functionality at a given point in time, such as a module to determine blood pressure, to determine weight (e.g. a connection to a scale), determine glucose level, and/or to track physical activity, among other functions. One example of connection slots in the device is a USB (Universal Serial Bus) connection, but any type of connectivity may be provided. For example, the device 200 may include a receiver or transceiver while a remote device or module may include a transmitter or transceiver, or the device 200 may include a connection slot for a receiver or transceiver, with connectivity to the device 200 provided via a slot, such as a USB slot.

Device 200 may provide wireless or wired connectivity, including reception of wireless signals or transmission of wireless signals, and may offer any other type of connectivity to a remote computing device as may be known in the art.

Figure 2B:
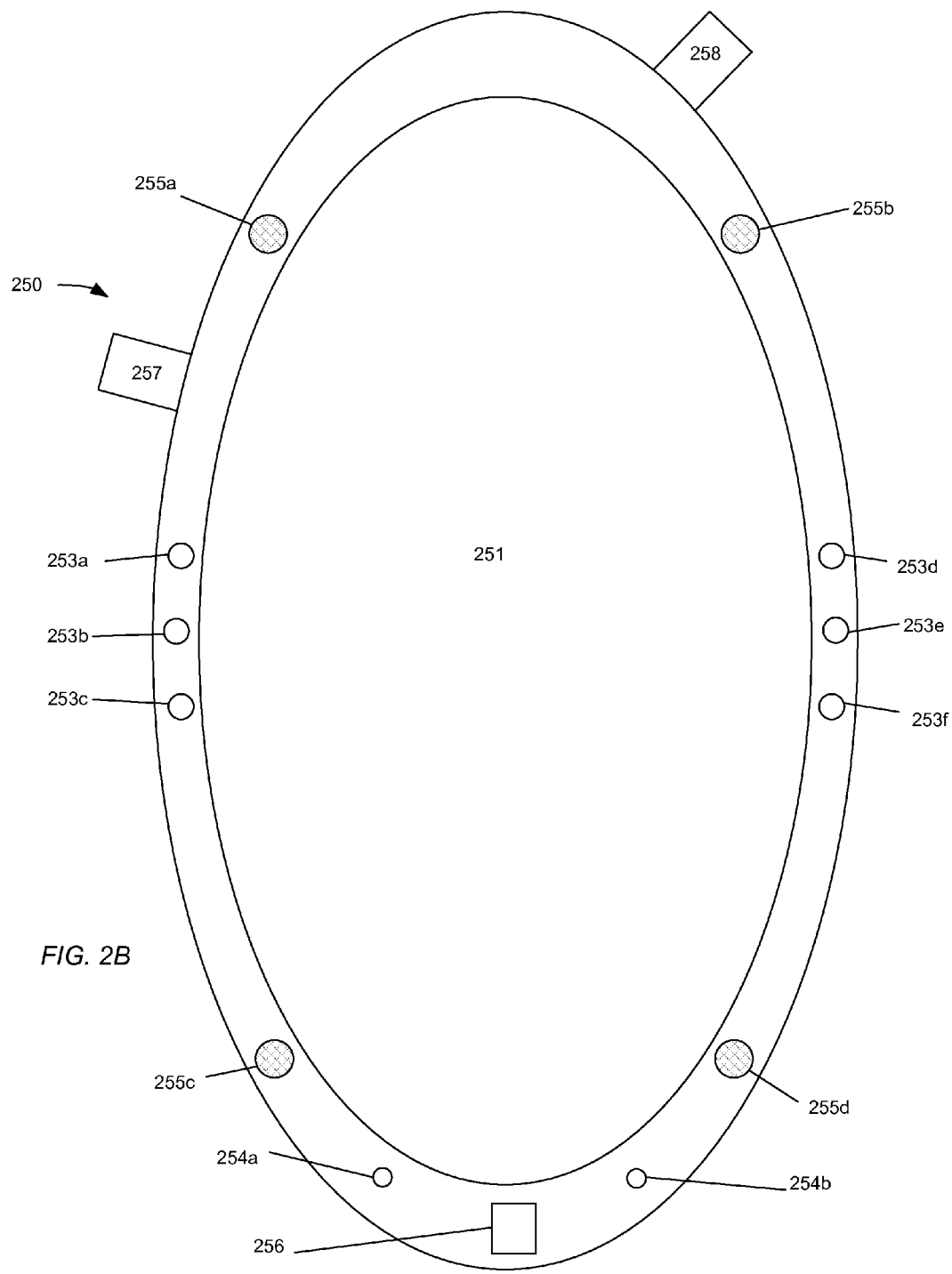
FIG. 2B illustrates an oval embodiment according to another aspect of the present design.

FIG. 2B illustrates an alternate embodiment of the device. The device 250 in the FIG. 2B embodiment is oval in shape, again with a central screen 251 that is both a mirror and a display. Edge element 252 may be provided and made from any suitable material, and cameras 253a-f, microphones 254a and 254b, speakers 255a-d, sensor, voice, or fingerprint reader 256 are provided. Also shown in this embodiment are two modules 257 and 258, each providing functionality as described herein. While a generally rectangular and a generally oval shape device is shown in FIGS. 2A and 2B, any form or type of device that provides the functionality described may be provided.

While shown as an integrated device in FIGS. 2A and 2B, it is to be understood that the present design may also include a conversion kit that may employ a plasma or LCD/LED television, including an outer frame that will be able to attach to the central screen and may include cameras, USB outlets and hardware such as a processor, storage, internet connectivity, and/or other pertinent functional components. A program may be provided that allows the user's television to operate in the manner discussed herein. Further, the present device may be incorporated into a piece of furniture, or into a wall, or into any type of other apparatus, either using the full device such as the embodiments shown in FIGS. 2A and 2B or as the aforementioned kit or part of the kit. The device may in various instances be mounted to a wall using mounting hardware known in the art.

Figure 3:
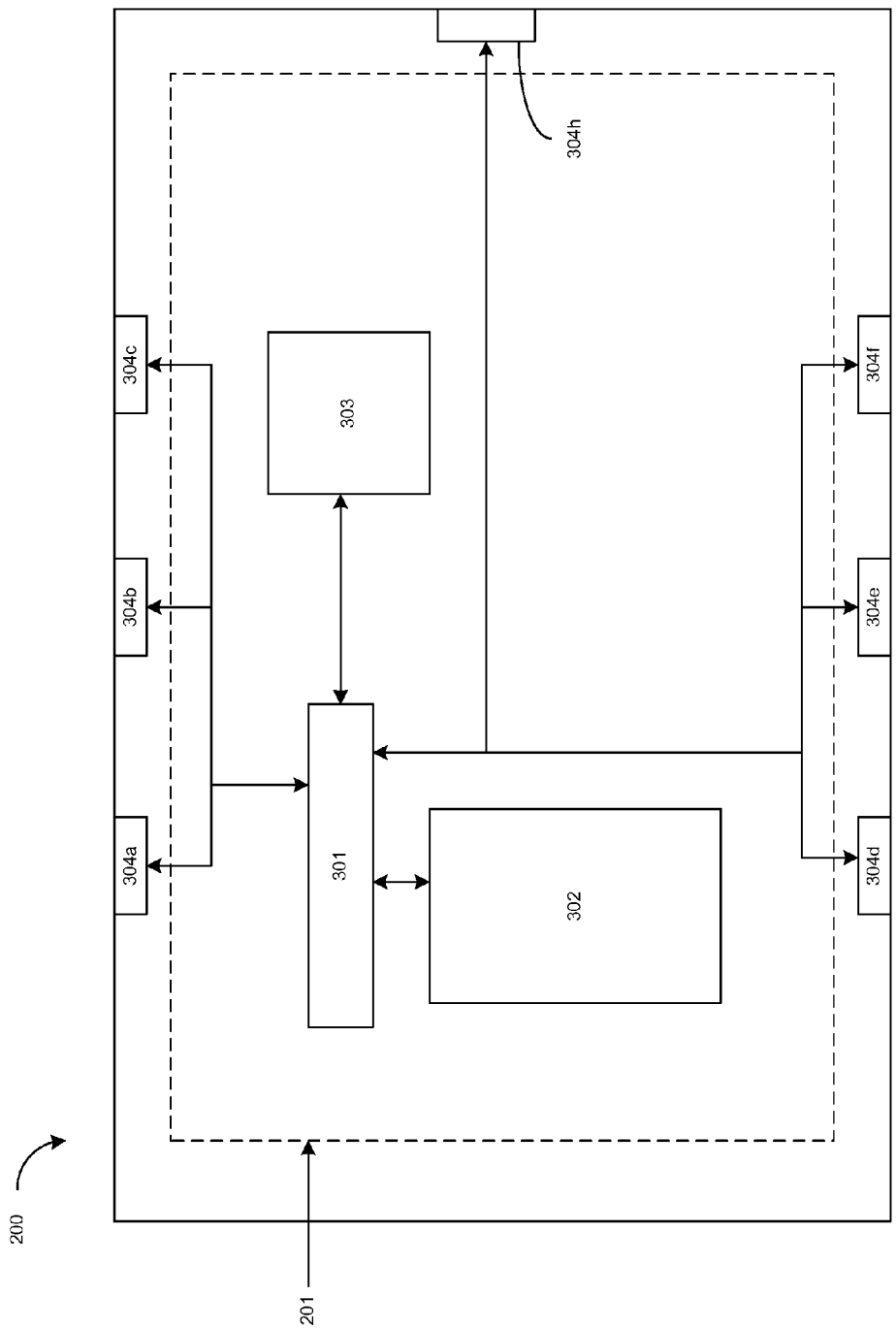
FIG. 3 is a general representation of certain components employed in the present design.

A general view of the electronics employed in the present design is shown in FIG. 3. From FIG. 3, device 200 includes a processor 301 connected to a storage device, such as a memory device 302, and is connected to display 201. The device may include wired or wireless connectivity, shown as element 303. Wireless signals may be transmitted from and received by the device and provided to the processor 301. Connections are provided to multiple connection slots, here shown as connection slots 304a-g. Any number of connection slots may be provided, and these may be USB slots or any type of connection to modules available in the art.

The device, such as device 200 or 250, may be open source in the sense that third parties may manufacture modules or module components that may interface with the device. Standards may be provided such that modules may be produced and desired functionality provided in conjunction with the device and its component parts. Further, the modules may be employed with devices already available, such as a blood pressure module used with an existing blood pressure cuff or other blood pressure evaluation apparatus.

FIG. 4A illustrates a side view of a device similar to that shown in FIG. 2A, where device 400 includes various openings or ports, such as USB ports, 402a-e. FIG. 4B is a rear view of an embodiment of the device 450, including an electrical connector 451 and a pill dispenser 452. The pill dispenser may be a removable feature and may be constructed to accept pills at a given time, with information provided to the processor as to how many and what type pills have been provided, and pills may be commanded to be dispensed by the processor, such as one pill per day if one pill per day is required. A handle 453 is provided such that the owner or some other individual can remove the dispenser or pull the dispenser out for purposes of restocking the dispenser. A tray 454 is provided such that pills or medications dispensed can be provided toward the front of the device and are easily accessible to the user.

Figure 5C:
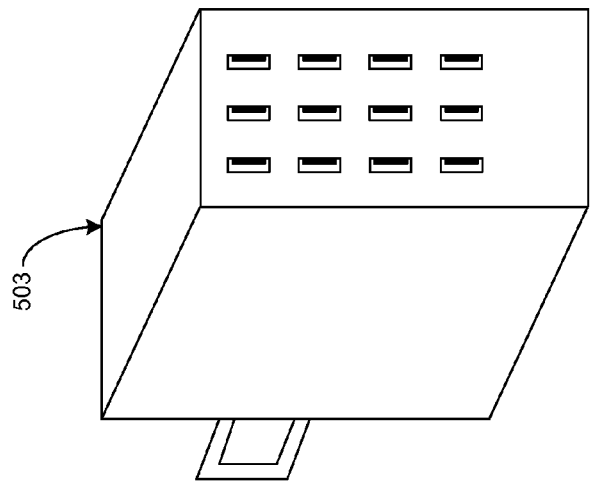
FIGS. 5A-5C illustrate apparatus including a set of separate USB receptacles that may be provided as an alternative to or in addition to the receptacles or slots provided on the device.
Figure 5B:
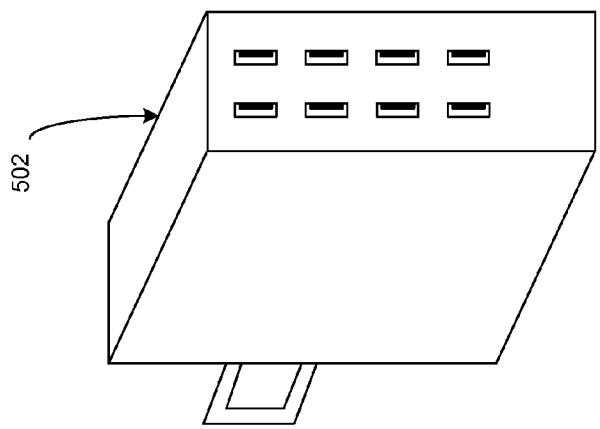
Figure 5A:
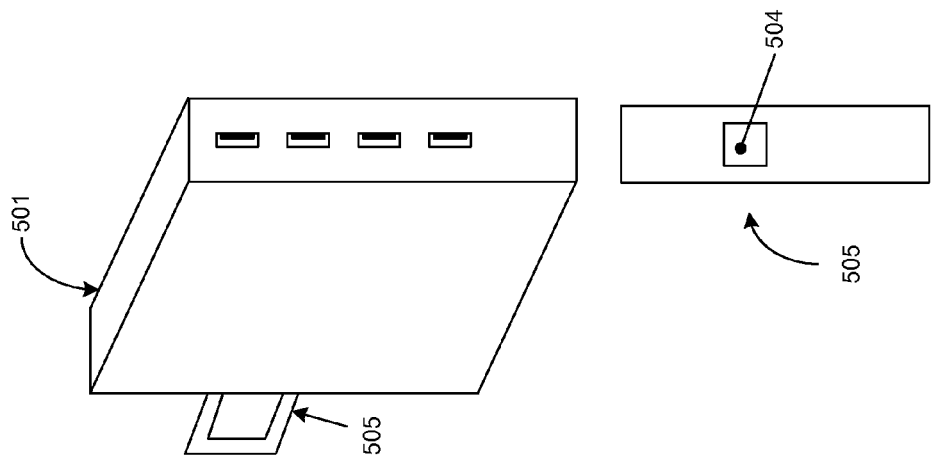

FIGS. 5A-5C illustrate apparatus including a set of separate USB receptacles that may be provided as an alternative to or in addition to the receptacles or slots provided on the device. The apparatus 501 of FIG. 5A, and the other apparatus 502 and 503 shown in FIGS. 5B and C, may be separate from the device and/or may connect to the device via wired or wireless communication. Apparatus 501 of FIG. 5A includes four ports or slots, apparatus 502 of FIG. 5B includes eight ports or slots, while apparatus 503 of FIG. 5C may include twelve ports or slots. Processing functionality may be provided in apparatus 501, 502, or 503, and the user may insert functional modules into the slots provided. Based on the module inserted, data may be collected, or data may be collected and transmitted to the device, such as device 200 in FIG. 2, for processing and/or further processing. As shown in bottom view 505 of FIG. 5A, a slot 504 may be provided for powering apparatus 501. The separate handheld unit described below may include port arrangements similar to those illustrated in FIGS. 5A to 5C, and a handle 505 or other carrying feature may be provided with the apparatus.

Figure 6:
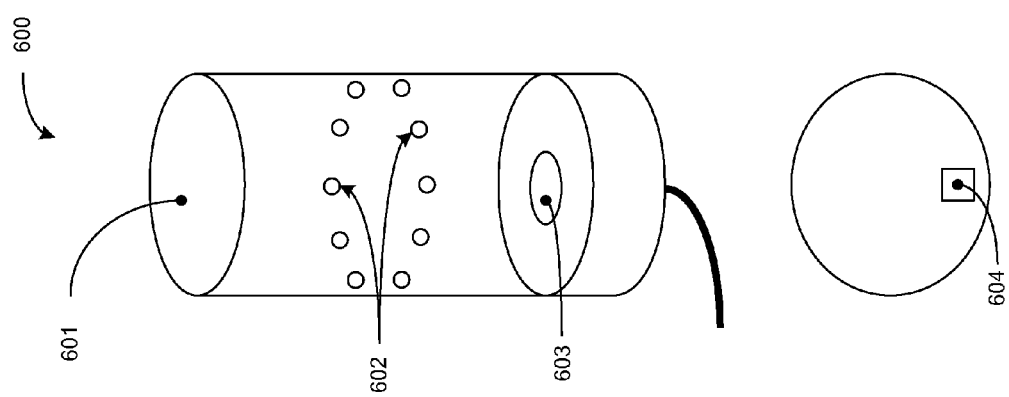
FIG. 6 illustrates an example of a magnification camera that may be employed with or provided as a module.

As may be appreciated, any number of functional personal care modules may be provided. As an example, devices to measure pulse rate, blood pressure, body temperature, and so forth may be provided, each with connectivity back to the device, such as device 200. FIG. 6 illustrates an example of a magnification camera 600 that may be provided for any number of uses, including but not limited to examining skin regions, oral examinations, and so forth. Magnification camera 600 includes an open area 601, a set of lights, such as LED (light emitting diode) lights 602 around the periphery of the interior of the magnification camera, and photographic element 603. The bottom view illustrates a port connection 604, such as a USB connection.

The device may be provided with a module or modules having an ability to read a barcode, including but not limited to a camera such as magnification camera 600. Any type of barcode or QR code or other code known in the art may be employed and may be read. Such scanning functionality enables the device to perform a variety of functions, including but not limited to reading prescription bottles, reading medical products, reading clothing tags and labels, reading cosmetics, reading containers of vitamins, and so forth.

Figure 7:
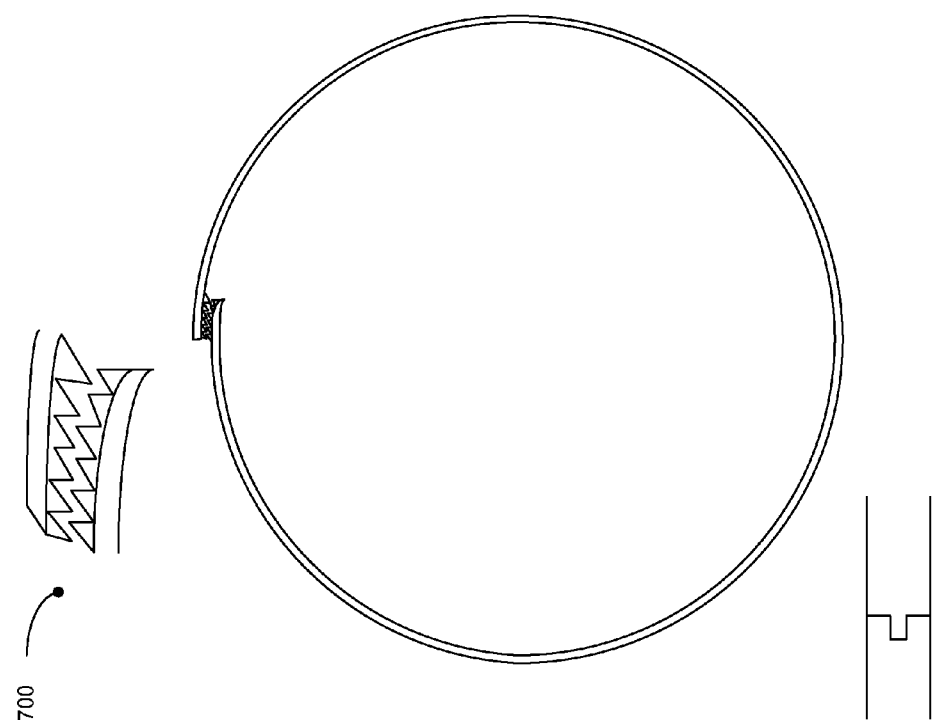
FIG. 7 illustrates an example of a sensing bracelet that may be employed with or provided as a module in accordance with the present design.
Figure 8:
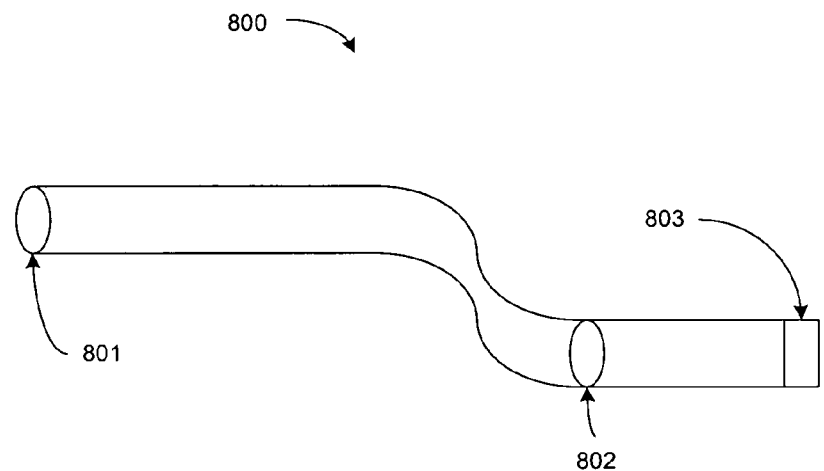
FIG. 8 illustrates a tape measure that may be employed as or in accordance with a module in the present design.

FIG. 7 illustrates an example of a sensing bracelet 700 that may be employed with a module in accordance with the present design. Sensing may be provided for pulse, temperature, and/or other pertinent measurements related to the individual. As an example, the sensing bracelet 700 may include lockable components such as teeth that enable resizing of the sensing bracelet 700. Sensing bracelet may also include a reflective coating or other marker enabling the device to sense the position of the bracelet and hence the user's arm. Such sensing capability may enhance the ability of the device to determine exercise performance and other pertinent information. FIG. 8 illustrates a tape measure 800 including a static reflective bead 801, an adjustable reflective bead 802, and a reflective position stop 803, enabling the measurement of anything, including but not limited to body parts, clothing, hair, separation of feet, and so forth. While FIGS. 7 and 8 do not include connections to modules or the main device, it is understood that such components may either be separate or may be connected by wire, or wirelessly (Bluetooth, etc.) to the device or a module as appropriate. In certain instances, minimal or no connection may be provided, such as no physical connection but an ability for the device, via microphone, camera, etc., to determine position of particular components. In FIG. 8, for example, tape measure 800 may not be connected by wire or wirelessly to a module or the device, but the device may employ a camera to determine positions of the static reflective bead 801, adjustable reflective bead 802, and/or reflective stop point 803 and use the measurement to determine the size of a desired object or objects.

Figure 9:
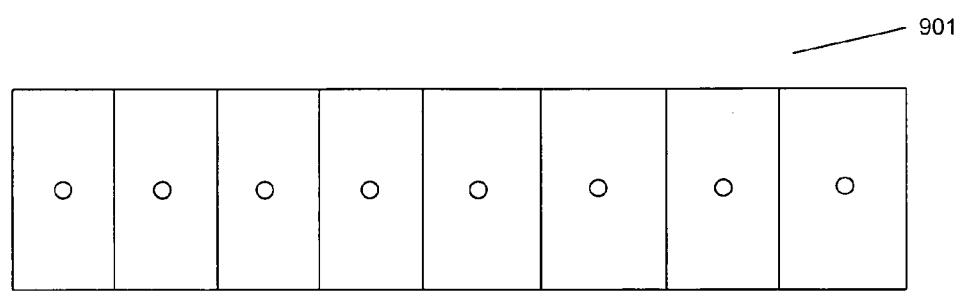
FIG. 9 is a reflective band or strap 901 that may be employed in association with a module.
Figure 11:
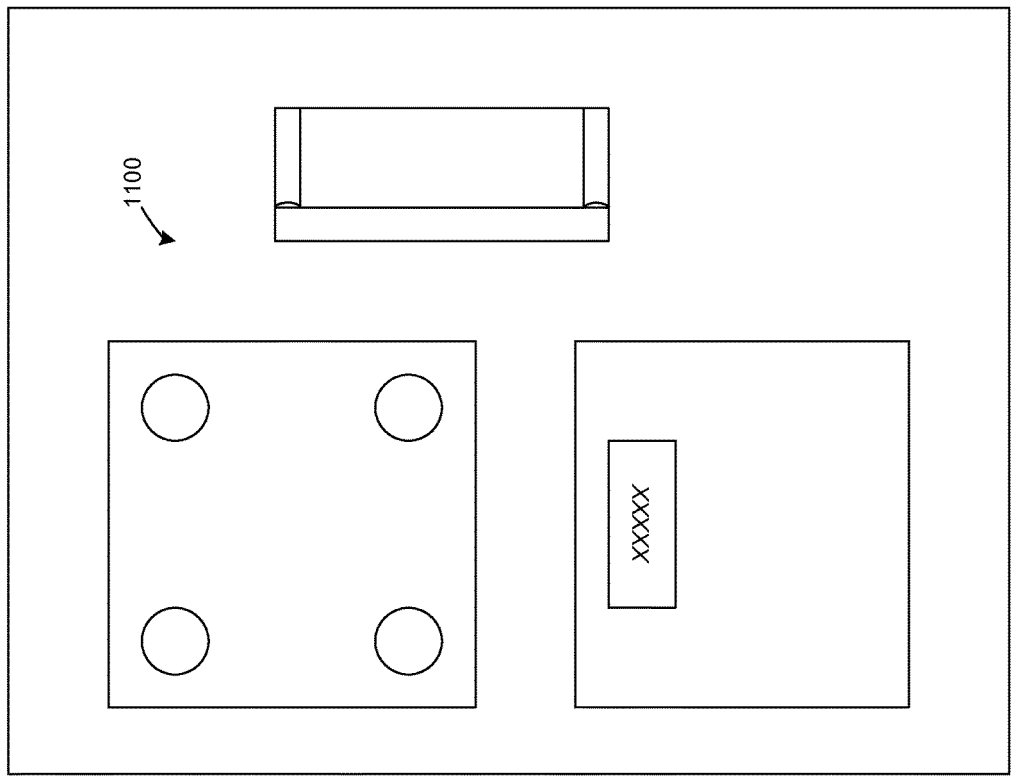
FIG. 11 illustrates a portable scale that may be used with the present design.
Figure 10:
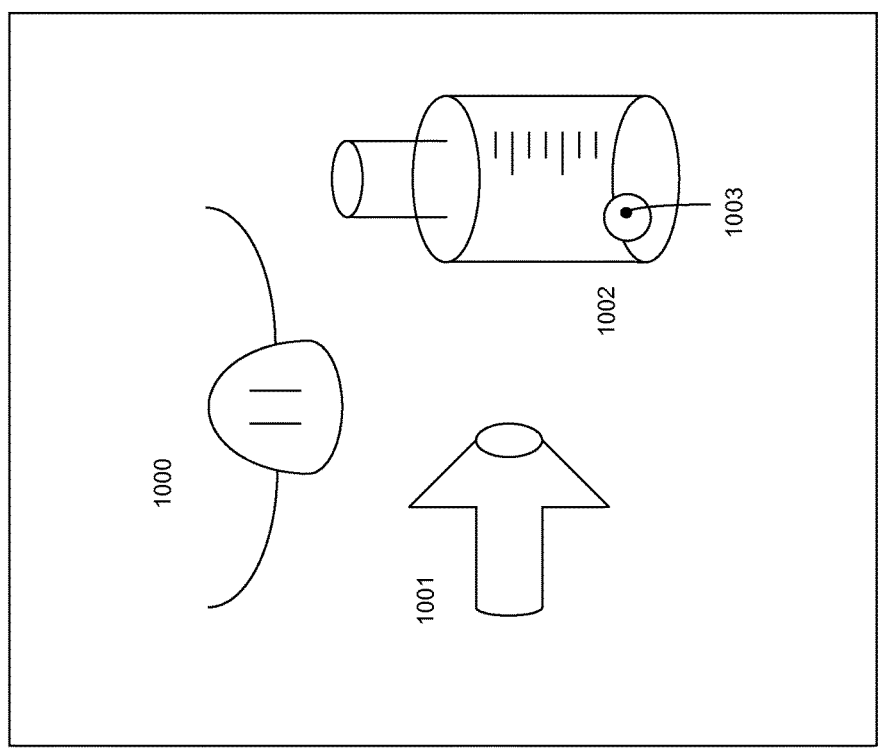
FIG. 10 shows a spirometer arrangement that may be employed as part of the present design.
Figure 12:
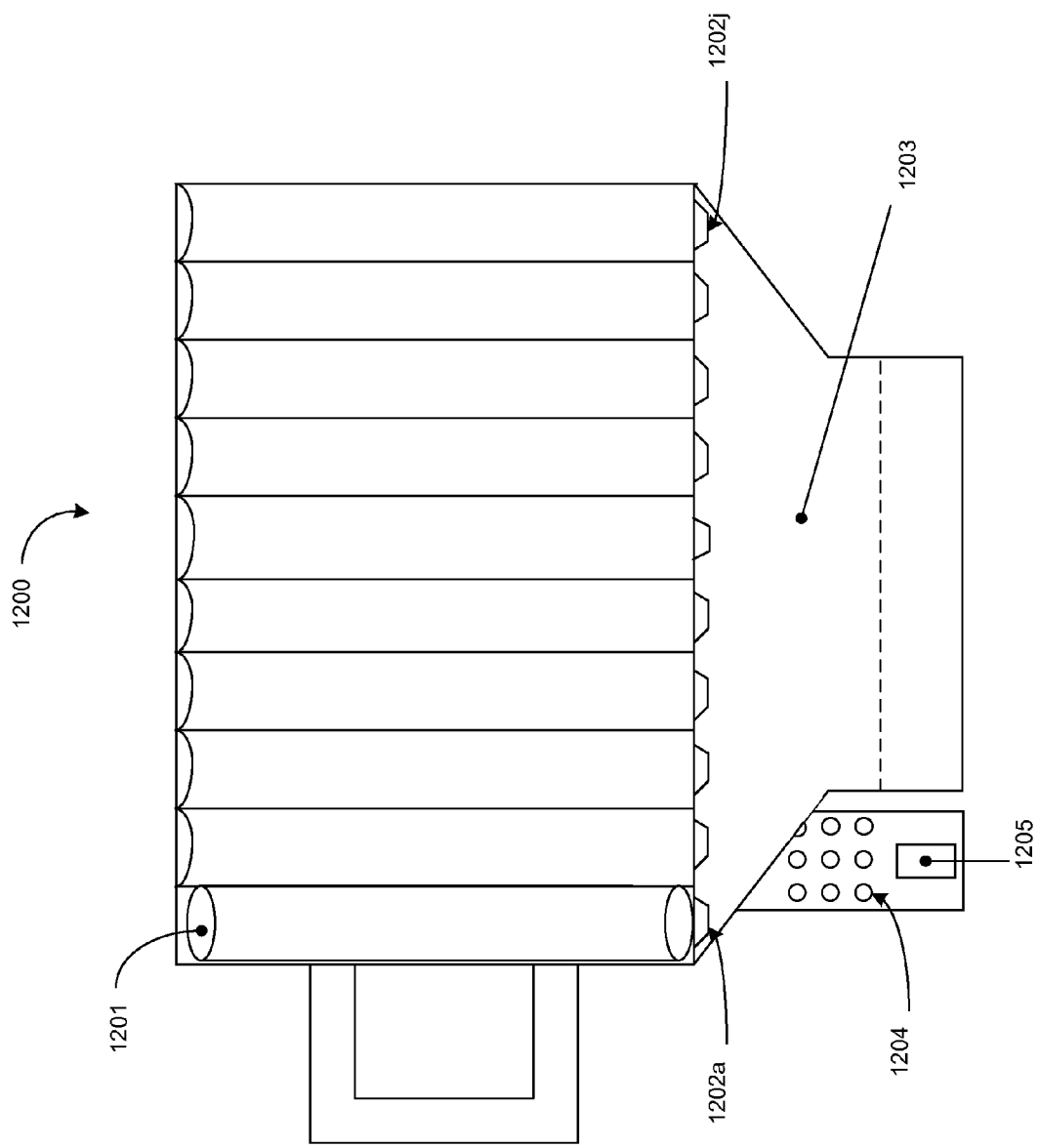
FIG. 12 is a pill dispenser that may be employed with the present design.

FIG. 9 illustrates a reflective band or strap 901 that may be used to measure head parameters, including temperature, EEG, sweat, and so forth, and may include massage beads. Reflective measuring markers, such as lines or points, may be provided. FIG. 10 illustrates a spirometer 1000, mouthpiece 1001, and a bottle or container 1002 marked with measurement markings, typically reflective, and including a measurement ball 1003, also typically reflective. FIG. 11 illustrates a portable scale 1100, employed to weigh applicable items. FIG. 12 illustrates a pill dispenser 1200, including a locked compartment 1201 for controlled substances, having programmable dispensing windows 1202a-g configured to control disbursement of pills, a tray or holder 1203, manual pill dispensing buttons 1204, and a fingerprint security reader 1205. The pill dispenser 1201 may be removed from the device and brought to a qualified individual, such as a pharmacist or pharmacist assistant, who can provide pills and/or controlled substances for use by the user. Sufficient security is provided, such as using fingerprint security reader 1205 or other device (sensor, voice recognition, etc.) and manual pill dispensing buttons 1204 and the programmable dispensing windows, where ten such programmable dispensing windows are shown in FIG. 12 and programmable dispensing windows 1202*a* and 12021 are identified. In this arrangement, the user and only the user or an individual identified as responsible for the user can obtain the necessary pills and/or medications. While shown as a pill dispenser, other forms may be taken to dispense bottles, a door that can be opened and closed with sensing provided, and/or other appropriate containment and disbursement hardware. Pill dispensing may entail the device reading a barcode label of the pills being inserted into pill dispenser 1200, and the device may receive and/or provide pill count, dosage, warnings and related indications.

Figure 13:
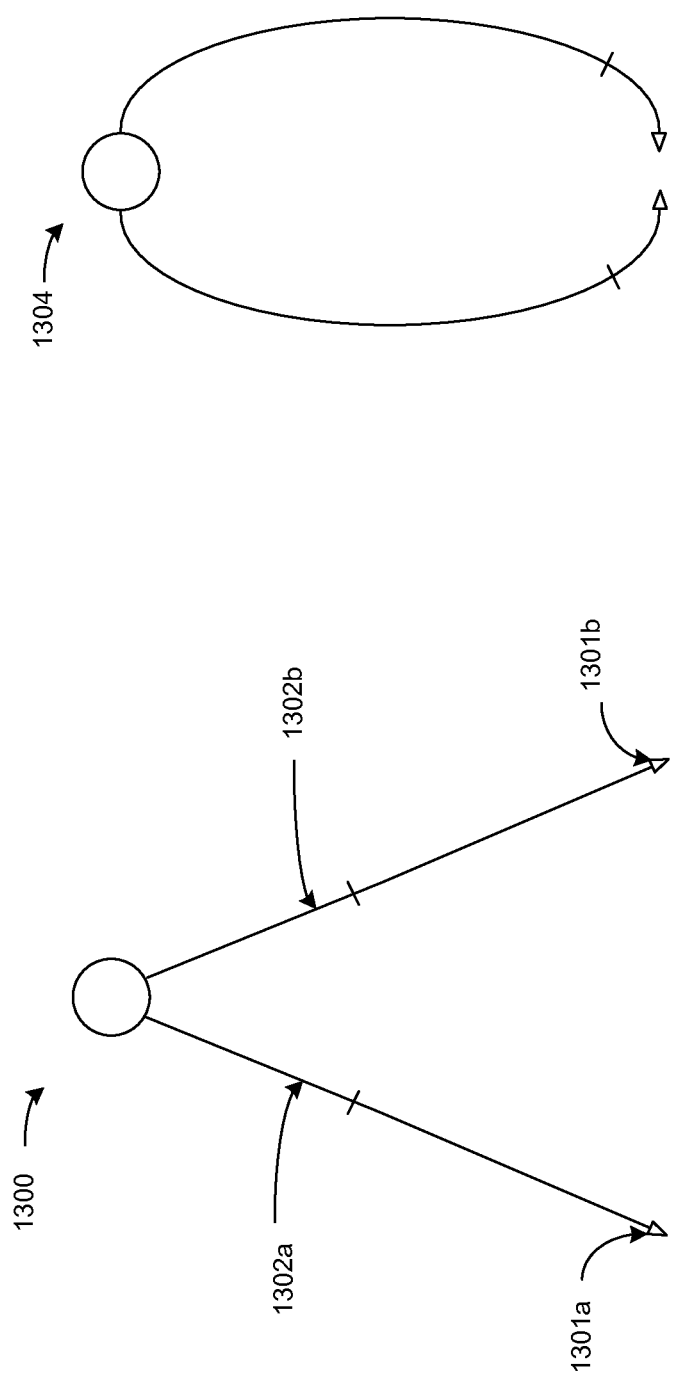
FIG. 13 shows a representative caliper that may be used with the present design.

FIG. 13 illustrates a representative caliper 1300, including reflective tips 1301*a* and 1301*b* and telescopic arms 1302*a* and 1302*b* meeting at jointed element 1303. An alternative caliper is shown as caliper 1304. Reflective points may be provided.

Figure 14:
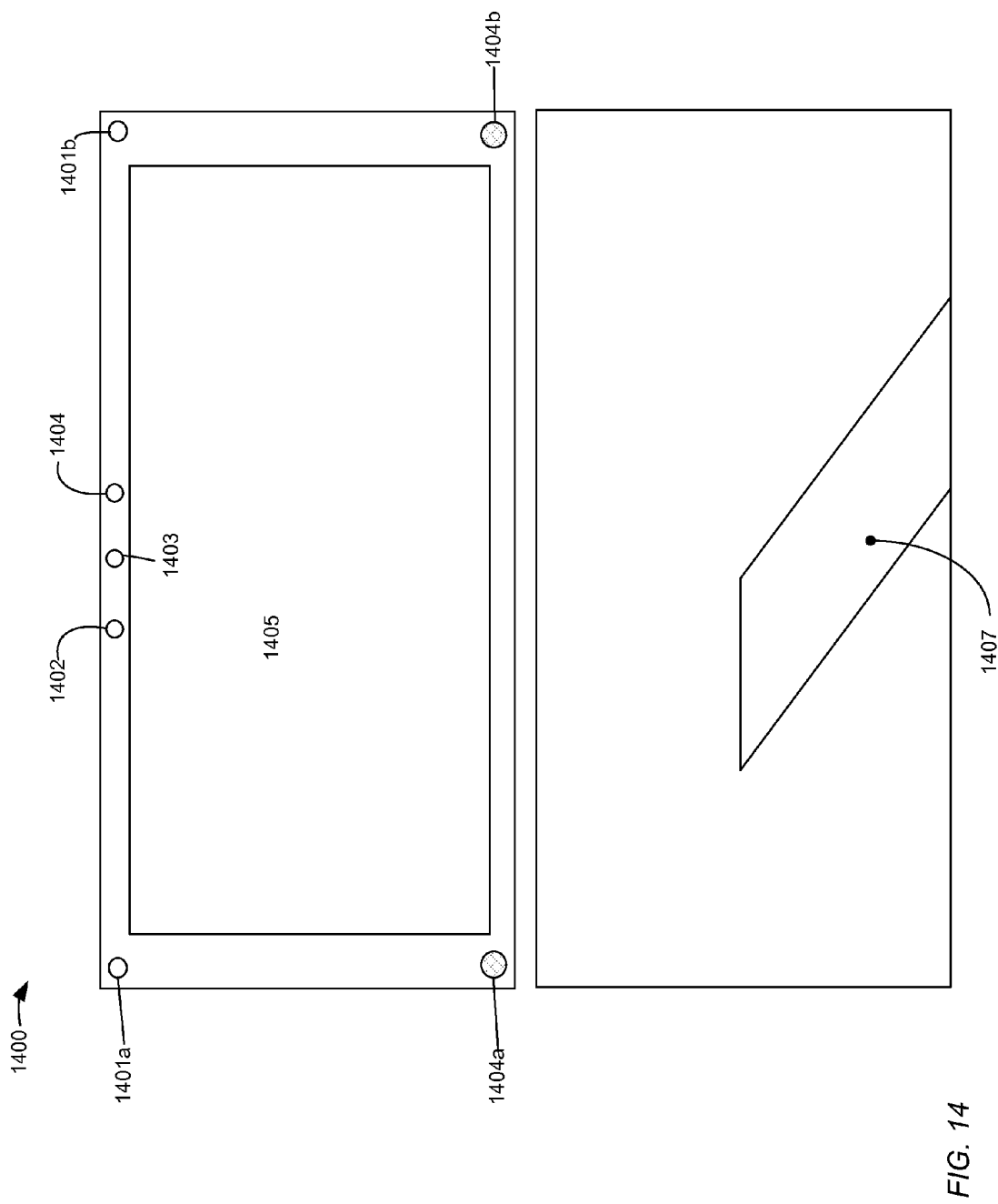
FIG. 14 illustrates a handheld unit that may be used with the present design.

FIG. 14 illustrates a handheld unit 1400. Handheld unit may be carried by the user or other appropriate person for various purposes, including but not limited to collecting data at a remote location, such as a gym, and/or transferring data to a remote location, such as a third party's computing device. Processing functionality is typically offered in the handheld unit 1400, and the handheld unit 1400 typically takes the form of a smartphone or other appropriate handheld device. As shown in FIG. 14, handheld unit 1400 includes a microphone or microphones 1401*a* and 1401*b*, a thermal camera 1402, a 3D camera 1403, and a biometric camera 1404, screen 1405 which may or may not be a mirror screen as with the device, and speakers 1406*a* and 1406*b*. Screen 1405 may be a touch screen or may be used as a sensor. On the back of the handheld unit 1400 may be provided a stand 1407. A sensor (not shown) similar to the sensor on the device may be provided for authentication purposes (fingerprint, voice, biometric, etc.), or the screen 1405 may be used as a sensor for authentication purposes.

Not shown is the ability of the handheld unit 1400 to connect wirelessly or by wire to either the internet, a cellular service, or other communication service, and the functionality provided may include the ability to collect user data and report the user data to the device and/or obtain user data from the device and/or a remote server or remote arrangement and convey the information to the user or provide the information to a third party. Data may be collected and downloaded at a later time to the device when within range of or communicatively connected to the device, such as device 200. Certain module connectivity may be provided such as via a port or connection.

The handheld unit 1400 may be incorporated into an existing device, such as an automobile part (armrest, headrest, dashboard, console, etc.) or airplane part (armrest, headrest, etc.) or any other type of device. The handheld unit 1400 may be incorporated into devices such as gym bags, purses, clothing (coats, etc.), or even pieces of furniture or other apparatus.

Additionally, but not shown in the foregoing illustrations, a keyboard, either hardware or software, may be provided with the device, such as device 200, or with the handheld unit 1400 such that the user may enter information, request processing, request uploading or downloading of information, and so forth.

Modules provided may include one or more of the following and/or any other combination of devices and/or functionality generally directed to personal care. Modules may include 3D camera-user recognition, recognition of the user using a three dimensional camera or multiple cameras (3D, planar, or holographic), enabling creation of an avatar or virtual avatar of the user, a thermal camera module configured to detect body heat of user, as well as user movements and health related temperatures, a biometric camera module, a scale similar to that shown in FIG. 11 to determine weight, fat, visceral fat, water and muscle content of user, and a heart monitor module configured to determine and provide the heart rate and ECG of the user, track activity of the user as well as changes in heart rate during exercise and/or for the purpose of providing medical alerts. Other modules may include a glucose meter to take blood sugar readings and track blood sugar of the user and may be employed with a medical alert, an oximeter or oximeters that monitors oxygen levels of the user, also possibly used in conjunction with a medical alert, and a blood pressure module that takes blood pressure readings and tracks user blood pressure and may be used with a medical alert. In the present design, connectivity to the device, such as device 200 is provided, and the modules may take any form, such as a small electronic component connected by wire or wirelessly or by any other functional connection to a device, such as in the case of a blood pressure monitor to a blood pressure cuff and inflation device, together with a sensor that senses the blood pressure once the cuff is inflated to the required level.

Medical alert and home alert capabilities may be provided as the device may listen for trigger words as "HELP" or "911." The device may also provide or be connected to a portable panic button.

Functionality and modules provided may also include retinae scanners enabling the identification of the user as well as monitoring eye health and changes, and a finger print reader or readers usable as a security feature and providing temperate reading and other health screening tests.

Modules may take any form, but as an example, they may be the approximate size of a modern car key module and may have a lithium or other appropriate battery in addition to the USB connectivity for both charging and data transmission purposes.

During operation, the present design may employ the video screen of the device and/or the portable unit to display graphical information, alerts, data collected from the modules and/or related devices and may provide information in the form of reminders or even commercials. The device may employ infrared reflectography using 3D laser scanning to create 3D topographical maps of different body parts (face, muscles, breast, feet, hands, teeth, and so forth) using either reflected infrared or lasers of different strengths. Different readings and different algorithms can be employed for different parts of the body, e.g. bumps and lumps on the skin surface, different angles of inclination, joint range of movement, and so forth.

Modules may be manually or automatically updated the user may choose, via the device, combinations of inputs into the modules. The device may provide face recognition capabilities and may be used to recognize third parties (family members, caregivers, pets) and may potentially be employed to sense intruders. The device may take on the attributes and functionality of a computing and/or communication device and may be placed in a sleep mode and awakened through voice activation or other audible communication, e.g. finger snap, clap, or even a button. The device can employ the cameras provided to track eye movement and/or focus on a certain part of the body, and may enlarge the body part or move it through certain ranges of motion. In the fashion area, a user may try on a piece of clothing and the screen of the device may ask the user to turn around and may show the user how the back of the garment appears. In the cosmetics area, cameras may record multiple versions of the same general skin area when the user employs different cosmetics on the area for the purpose of allowing the user to compare and contrast different cosmetics.

The device typically operates using an open platform that integrates data input and reception in conjunction with applications specifically designed for the device. When using the handheld unit 1400, the user may have available a portable accessory to carry one or more modules, such as a glucometer module if eating or a fitness module (measuring heart rate, movement, etc.) if going to the gym.

In operation, user interaction with the device and/or modules may entail the collection of data that may be retained at the device, with data provided from modules to the device via WiFi, Bluetooth, or through a USB connection or by any other means known in the art. The processor at the device may process the data using device formulas and/or applications and may format the data into graphs, charts, diagrams, virtual assistants and other forms to be displayed to the user via, for example, the device (2D, 3D, or holographic) screen. The data and/or information may be controlled by the user and may be sent from the device, such as device 200, to a remote location, i.e. a virtual "cloud," where the information may be collected, analyzed, and/or stored. Once transmitted to the remote devices, the user information may be maintained, analyzed, and specific user recommendations or information may be transmitted back to the user. As currently configured, varying levels of service may be provided. As one example, a gold/silver/bronze level of service may be provided, wherein bronze is simply maintaining data at a remote site, silver is analyzing data and providing recommendations, and gold is a concierge type service where the user may be provided contact with available personnel (physicians, pharmacists, personal shoppers, cosmetics specialists, optometrists, dentists, etc.) and particular needs will be addressed. Different or alternate levels of service may be provided.

As may be appreciated, virtually any type of information may be collected and/or provided using the device/module arrangement provided herein. The ability for the user to indicate specific needs and desires via a keyboard and possibly a mouse, and for the device to display information and act as a mirror enables a virtually unlimited range of functions. A particular user may wish to receive clothing recommendations, and may have her skin tone and hair color determined, and clothing color recommendations provided. Body type may be determined, and age entered, and age appropriate wardrobe selections may be provided based on an analysis provided from the remote location. Another user may have a blood sugar issue, and his blood sugar may be monitored and tracked, and based on his history and desires, recommendations as to what to eat and/or when to eat may be provided to the device and/or to the handheld unit 1400. Another user may want to monitor stock quotes and baseball scores in addition to tracking his progress on a weight loss program. While providing stock quotes and baseball scores is not strictly a personal care function, the present design may offer any type of functionality offered by a computing device and/or tablet and/or smartphone. Thus the user may be exercising with the handheld unit 1400 tracking his progress, i.e. time spent exercising on a treadmill, while the device may display stock quotes or baseball scores. At the end of the user's workout, he may weigh himself using the scale module and may receive meal recommendations and/or a graph of his exercise progress or weight via the device. Thus single or multiple functions and determinations may be provided or made based on functions, applications, and computations available, as well as the needs and desires of the user, in addition to the functionality provided at the remote device arrangement.

Figure 15:
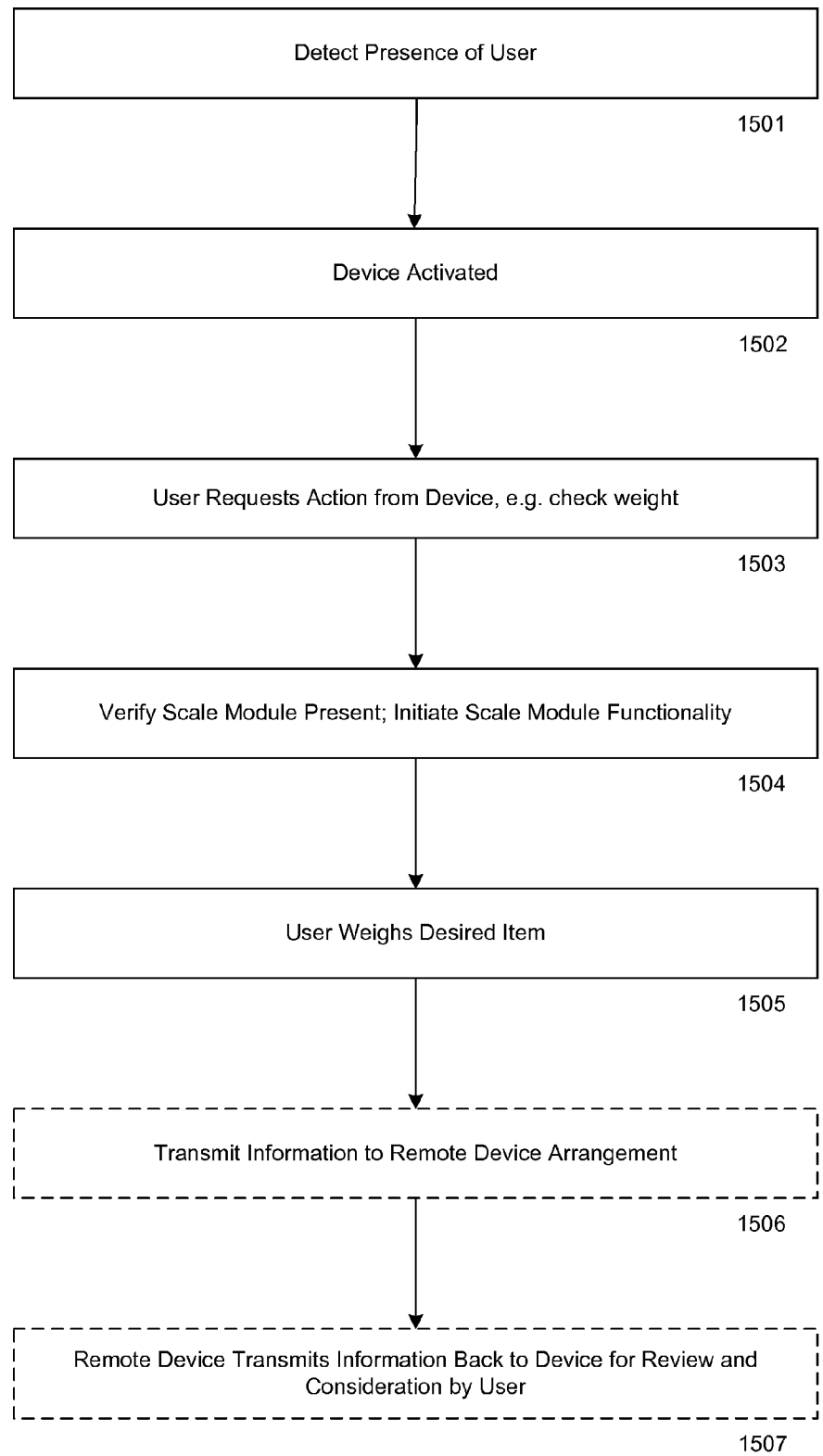
FIG. 15 is a simple functional example/flow diagram of use of a scale module.

A simple functional example of use of a scale module is presented in FIG. 15. From FIG. 15, the device, and more specifically the cameras on the device or the fingerprint reader or other device component, detects presence of the user (e.g. pressing a key on a connected keyboard) at point 1501. At point 1502, the device, such as device 200, is activated and may come out of a sleep or hibernation state as appropriate. At point 1503, the user may ask for an action from the device, in this case checking the weight of a desired item using a scale. The device determines whether the appropriate module is connected or available, here the portable scale module. If not, the device prompts the user to connect the module to the device, and the scale module functionality is initiated as shown in point 1504. Weight information may be provided on the screen of the device, and specific information may be provided—commercials, recommendations, graphs of weight readings over time, most recent weight, and/or other information.

At point 1505, the user weighs the desired item, and the resultant weight is provided to the device, and more specifically the processor in the device. The screen of the device may display current weight and tracked weight, either graphically or numerically. At point 1506, which is optional, the device, such as device 200, may transmit the information to a remote device arrangement for further processing, such as determining recommendations for a man the user's age and in the user's situation. At point 1507, the remote device arrangement may send user specific information back to the device, such as device 200, for review and consideration by the user. Emails, text messages, phone messages, and/or other user selected communication methods may be employed to inform the user of determinations made at the remote device arrangement. Certain information may be provided from the remote device arrangement to the device to enhance operation, such as locally storing recommendations for the particular user determined at the remote device arrangement. The device may at that point return to a hibernate or sleep mode or may continue operation as desired.

Functions may vary and may depend on what is required, and as may be appreciated, any list of functions may be changed, improved, reduced, or otherwise altered depending on a variety of factors, including but not limited to popularity of the functions, needs and desires expressed by users, use patterns, costs associated with apps and functions, and so forth. Certain functions may be provided either locally, i.e. at the device, or remotely, i.e. at the remote device arrangement, or a combination of both. In general, the system, including the device and remote device arrangement, receive information and queries and respond appropriately for personal care issues that arise.

Examples of the determinations made and functions provided are as follows. In the area of health, lung health may be maintained and monitored, and the device may determine respiratory rate (RR), $CO_2$ level, lung volume, pulse oximetry, breathing characteristics, jugular vein distension (JVD), pitting edema, and/or body pH level. The device may respond with a chart including a degree of hypoxia, a graph with the user's lung volume as compared to users of similar age and sex, and a pitting edema score. In the area of heart health, the device may collect pulse/heart rate, blood pressure, heart rhythm, and EKG values with appropriate modules. The device may determine and/or report a graph, raw data, and or percentile data, as well as recommendations. In the area of nose and sinus health, the system, including the device, handheld unit, appropriate modules, and/or remote device arrangement, may analyze the nose for deviations in shape and/or color, flaring, discharge, and nasal patency. The system may then provide raw data, a digital model of the nose and/or sinus, and provide a percentile, score, and/or chart. In the field of eye health, the system may assess or determine sclera color, visual acuity, peripheral vision, analyze the pupil, iris, sclera, and so forth, determine eye pressure, redness or dryness, and eyelash evenness, and the system may provide a digital model of the eye, a scoring of quantities such as peripheral vision, raw data, percentile values, a chart, and a chart or graph.

Many, if not all, of the health related evaluations may result in a combination of a score or scores, raw data, percentile, and a chart or graph of the health of the particular site. It is to be understood that these and other relevant information (recommendations, warnings, pictures, etc.) may be determined and provided as appropriate, but that all such determinations may be made and provided when assessing health parameters.

In the area of ear health, the system, again including the device, handheld unit, appropriate modules, and/or remote device arrangement, may assess the internal ear, including the external, middle, and/or inner ear, analyze the external ear (auricle and pinna), determine degree of hearing loss, and perform a bone conduction evaluation (Weber/Rinne). Dental or oral care health may include an assessment of lips, inner and buccal mucosa, tongue, mouth floor, teeth and gums, hard and soft palate, salivary glands, and tonsils. Many of the assessments discussed may be made using a camera or recording device, but others may require modules specially made for the task. Digestive health may be assessed using food intake, stool analysis, BMI (body mass index), and weight. Liver health may be assessed using skin color, sclera color, ammonia levels in urine, level of consciousness, abdominal distension, weight, total body water, skin irritation, activity level, and/or stool color. General hormone balance may be assessed according to a hormonal profile, activity level, weight gain, EKG, heart rate, mood, level of anxiety, headaches, and/or sleep pattern. Kidney health may be assessed according to daily urine output, blood pressure, glucose level, and/or degree of edema. Muscle health may be assessed according to strength, tone, size, symmetry, fasciculations, tremors, arm/leg circumference, and activity tolerance.

In the present design, the user may be monitored using a module or the user may be queried directly or may offer the information requested. For example, the user may be queried as to "have you experienced any muscular tremors in the last week" and she may respond "no." Alternately, the user may be asked "what has been your activity level in the last day?" and may provide the user with options (none, mild, moderate, extensive, or quantities, such as ran for 20 minutes). Various options regarding obtaining the necessary information, including the necessary health information, may be provided. The user does not need to provide the information—the information may be provided by a third party (caregiver, spouse, etc.)

Nail health may also be assessed, analyzing convex curvature, i.e. the angle between the nail and the nail bed, and in addition to the other reports and/or information provided to the user, he may receive a graph of a degree of clubbing (normal, early, or late), based on nail bed shape and angle. Testicular health may be assessed according to a pain scale, new lumps, heaviness in scrotum region, and/or testicular swelling. Obstetric health maybe assessed—weight, heart rate, blood pressure, portable ultrasound results, fetal heart rate assessment and analysis, and food intake, for example. Bone health may be assessed according to bone density, calcium level, activity level, pain scale, swelling, nutritional intake, and a bone densitometer score. Mental health may be determined by assessing speech recognition, level of consciousness (LOC), weakness on one side, blood pressure, visual changes, and/or NIH score. Ovulation health may be assessed by determining a surge in Luteinizing Hormone (LH) urine, analyzing cervical mucus consistency and/or basal body temperature (BBT). In addition to the other health information provided (raw data, graphs, charts, etc., ovulation results may include a digital calendar or listing of best ovulation times.

Spine health may be assessed according to structures or deformities, warmth, swelling, range of motion (ROM), presence of scoliosis, and gait. Joint health may be assessed by evaluating warmth to the area, ROM, swelling, presence of nodules, and/or gait. Skin health may be assessed according to skin turgor, color, skin breakdown, and degree of edema. Hair health may be assessed according to hair distribution, hair density, color, moisture content, dryness, texture, and presence of infection and/or infestation. Breast health may be determined based on swelling around the breast and armpit, pain level, changes to nipple, discharge, signs of lumps, and/or menstrual cycle issues. Information provided relative to breast health may additionally include a video showing a proper breast exam, and a digital model of the breast of the user or a hypothetical breast, again for examination purposes.

Foot health may be determined by collecting signs of infection, color, hair distribution, skin integrity, and degree of pitting or edema. In addition to the other reporting data, the system may provide a digital model of feet or the lower extremities. A general collection of parameters for the user may occur, including but not limited to collecting heart rate (HR), temperature (T), basal body temperature (BBT), respiratory rate (RR), SaO2, pulse oximetry, CO2, systolic blood pressure (SBP), diastolic blood pressure (DBP), urine chemistry, dry blood work, joint ROM, spine flexibility, muscle strength, BMI, total body water (as a percentage of body weight) in relation to age and sex, electrocardiogram (EKG), lung capacity (TV, TLC, VC, FRC, RV), height and weight, and body pH level. These and other pertinent values may be collected and reported and/or continuously tracked.

In the area of fitness and wellness, different module specific interactions may occur where data is received by the system (device, handheld unit, remote device arrangement, module(s)) and certain information assessed and provided. In the area of fitness, the system may collect or receive user goals, weight loss values (current or desired), general fitness, preparation for an athletic event, muscle building, and rehabilitation from injury. Output may include an individualized fitness program as well as graphs and charts and recommendations. In the area of body building, height, weight, neck, chest, upper arm, waist, hips, and any other relevant area may be measured, and information about body fat provided as well as changes in body measurements. For sweat, the device may be provided with a module that analyzes user sweat and provides information on total free amino acids, ammonia, protein concentrations, and nitrogen balance of the user, detects a negative nitrogen balance, gives dietary recommendations, recommends post workout recovery meals, and recommends a dietary and supplement plan. For workout performance, the system, and possibly a module in the system, analyzes body mechanics during exercise by measuring weight distribution, relative angles at joints during exercise or body heat via thermal infrared camera. The device provides corrective user feedback on proper body mechanics during exercise. In the area of nutrition, the user may input daily food intake via picture, barcode scanner, or may select items consumed from a pull-down menu. Also provided or calculated are total calories, protein, carbohydrates, fat, and fiber. The system may recommend dietary changes toward fitness goals and may provide charts and graphs.

In the area of exercise, the system may collect or receive user submitted photos of gym equipment (at home or in gym), may enable interaction with an AI Personal Trainer, where the user communicates in real time with the AI Personal Trainer, time between sets, number of reps and weight lifted, body posture via angle of shoulders to waist and feet, and the system may recognize available equipment and build an exercise program. A trainer may observe the user while completing exercises and give real time feedback about technique. The system may provide motivational instruction. Recommendations by the AI Personal Trainer may optimize user exercise output. Physical health at work may be assessed by calculating angle of the body while seated and doing work, assuming the device or handheld unit is available at a representative workplace. The system may also calculate height of desk, chair, keyboard, and mouse. The system may recommend corrective body posture and ergonomic corrections to the work station. Physical health in the case of injury may be assessed, wherein a provider or the user or other appropriate individual may input the user's injury or injuries. The device may then create an exercise regimen based on the user's needs and specific injury.

In the wellness area of sleep architecture, the system may measure room temperature, amount of room light, noise, track user sleep/wake cycle, and the amount of movement during sleep. The system may recommend changes to sleep architecture. Tracks changes and saves users optimum sleep requirements. The system may also address menses, determining date of first day of the menstrual cycle, length of bleeding, bleeding volume, daily temperature, and may provide recommended dietary changes.

With respect to fashion, the system may assess body shape measurements, i.e. biometric points, body shape, and may measure four separate points—shoulders and hips, in the form of an "X." The system, including but not limited to the remote device arrangement, may provide recommendations on clothing style and cut, perform "body blocking," and provide a "virtual 3D mannequin" of the user based on calculations. The user may be allowed to "try on" various styles/cuts/colors of clothing on the virtual mannequin. Based on mannequin sizes, retailers will have better information on the user's particular clothing needs and wants. The system may also assess secondary body measurements, determining height, weight, BMI, arm length, arm circumference, thigh circumference, torso length (long, short, average), breast size, shoe size/width. From these secondary body measurements, the system may determine detailed body composition, make specific suggestions as to clothing, styles, and accessories through the device and available from retailers, and creation of a "virtual mannequin" can increase details known about the user's body image to both the user and a retailer. The system may also determine body size changes, assessing minor and major changes in weight and body changes due to pregnancy, and providing revisions or potential revisions to style, size, color, and cut of clothing, as well as suggestions.

The system may also assess user demographic information, such as age, race, geographic location, profession, income, education, marital status, and number of children. From this, the system can determine a presentation specifically tailored to the user, determine style suggestions, price points, and clothing styles relating to seasons, temperatures, and precipitation, and allows retailers to focus on a specific consumer profile. The system may additionally determine clothing wear, possibly employing a sensor in user clothing, to determine date of wear, number of wearings, and frequency of wearings.

With respect to cosmetics, the system may assess tone and pigmentation by determining skin undertone based on the color of the major vein around the wrist and by blue, yellow, red content against a white background. Results determined may include a 3D graph, a personal color wheel for hair, a personal color wheel for make-up, prescription skin care recommendations, over-the-counter skin care recommendations, peel recommendation, laser resurfacing options, and continuous updates and recommendations. Skin category may be assessed, including determining consumer inputs, oil content of skin, and reflexive skin properties, and providing a graph of skin, oily to dry, recommended moisturizing and cleansing creams. The system may also evaluate pores, determining distribution and spread measured by number per square centimeter and measure color and size of pores. From this information, the system may provide information including a graph, chart, updates and recommendations, microdermabrasion, chemical peels, facial cleansers, and creams.

Acne may be assessed according to distribution and spread measured by number per square centimeter, measurement of color and size of pores, acne location via a topographical map of the user's face, depth and height, and cystic versus black head. Information provided and reported may include a graph, chart, topography, updates and recommendations, microdermabrasion, chemical peels, facial cleansers, creams, laser resurfacing, and information regarding or from a dermatologist. Scars may be assessed based on discoloration, size, location, depth, and height. Again, based on this, the system may recommend or provide a graph, chart, topography, updates and recommendations, microdermabrasion, chemical peels, facial cleansers, creams, laser resurfacing, and information regarding or from a dermatologist. Skin elasticity may be assessed based on skin turgor, muscle and skin laxity, and nasolabial fold measurement. The user may be provided with a graph, topography, charts, updates and recommendations related to skin elasticity, firming products, and/or laser tightening methods.

Wrinkles may be assessed based on measurements of crow's feet around the eye, length, depth and quantity of wrinkles in particular regions, frown lines, forehead wrinkles, wrinkles around the mouth, wherein all wrinkles may be assessed based on wrinkles per square inch. The system may determine and provide a graph, chart, topography, updates and recommendations, cosmetic grade skin care, medical grade skin care, Botox treatments, fillers, chemical peels, and/or specialized laser procedures. As may be appreciated, more severe skin issues may call for added recommendations, procedures, products, and/or treatments.

Facial hair may also be addressed by determining follicles per square inch, coarseness, length, diameter, color, and/or location, and the system may provide graphs, charts, updates, and recommendations relating to waxing, medicated creams, and laser hair removal. Facial attributes may be assessed and recommendations or information provided. Facial attributes evaluated include shape, position of eyebrows relative to eyes, distance from medial eyebrow to medial canthus, distance from lateral eyebrow to lateral canthus, distance of lateral canthus to medial canthus, spread and distribution of hair per square millimeter, length and diameter of hair, shape and contour of eyes, diameter of iris, distance measurements of eyebrows, ridge of nose, and forehead/hairline, width of eyelids, distance of the upper eyelid from the lower lid at multiple locations, eye color-measure by the three basic color red, blue, yellow, color and discolorations of sclera, eyelashes measured by follicles per square millimeter, coarseness measured by the length, and diameter of each hair, with information provided including graphs, charts, topography, updates, and recommendations regarding shaping, make up, medications, Botox, and even surgery.

Facial symmetry of hair may be assessed, determining length of forehead and measurement of trichion to glabella. The system may recommend facial hair profiles and may provide graphs, charts, and updates. General face shape may be assessed, including measurements of trichion to menton, ear lobe to ear lobe, trichion to glabella, trichion to arch of eyebrows, infratip of nose to menton, menton to mandible, mandible to pre auricular points, and/or length of filtrum. Results provided may include graphs, charts, topography (as used herein, topography includes maps and or data related to topography of the particular feature(s) or region), updates, and recommendations including hair, make up, and jewelry.

Measurements and determinations of particular features may be made, including but not limited to nose, lips, cheeks, jaw lines, chin, and neck, with assessments made using cameras and any other appropriate devices or modules. Graphs, charts, topographies, and updates may be provided as well as feature specific recommendations, such as makeup, surgical procedures, makeup, fillers, moisturizers, treatments (e.g. Botox), and so forth.

Teeth may also be assessed based on measurement of teeth size, separation distance of teeth, angle of teeth, color or shade, and/or color of gums (measured by red, blue, and yellow against white). In this cosmetics area, other outside factors may be assessed—current medications and/or current diagnoses, for example. The system may make specialized recommendations pertaining to skin health with these medications and diagnoses, and may make recommendations of supplements and/or foods to maintain skin health.

Certain personality factors may be determined, such as desired look during the day or night, age, gender, geographical location, income, and/or occupation. From this, the system may determine graphs and charts, and may make recommendations such as color pallets and application instructions.

In the area of pharmaceuticals, the present system may make additional assessments and may determine recommendations and provide information to assist the user in his or her personal care. One area is prescription medications, wherein the system collects user name, quantity, dose, administration, duration of usage, refills, adverse reactions, use in specific populations, over dosage symptoms, over dosage signs, prescriber name, prescriber address, prescriber phone number, pharmacy name, pharmacy address, pharmacy phone number, controlled substance schedule (if applicable), price per unit, and medication expiration date. Certain information may be collected from third party sources if available, as is the case with other functions performed by the system. For example, if the medication is known, the system may submit a query seeking adverse reactions, or if a pharmacist is known, the system may seek the address and telephone number of the pharmacy from an online source. As may be appreciated, such specialized functionality must be provided in the system, i.e. seeking information from a particular site, seeking the specific information needed, and obtaining the information. The device may perform this functionality, or such functionality may be performed by the remote device arrangement or a person associated with the remote device arrangement.

Information provided by the system may include a drug interactions alert, a refill alert, alternative medications options, generic medication options, an electronic update of current medication list to the device cloud, filling of the pill dispenser, lock filling into medication drawers if applicable, providing alternative price per unit information from other suppliers, an expiration date alert, and a next dose alert through cloud based system.

Over the counter supplements and supplies may also be assessed and information provided. Assessments may include name, quantity, dose, administration, duration of usage, refills, adverse reactions, use in specific populations, over dosage symptoms, over dosage signs, prescriber name, prescriber address, prescriber phone number, store name, store address, store phone number, price per unit, and/or expiration date. The information provided to the user may include a supplement interactions alert, a refill alert, alternative supplement options, an electronic update of current medication list, filling of a dispenser, alternative price per unit from other suppliers, and/or coupon options from suppliers.

Health markers may also be assessed. Information assessed may include Indication(s) for particular drugs (allergies, etc.), heart rate, temperature, respiratory rate, pulse oximetry, systolic blood pressure, diastolic blood pressure, urine analysis, blood analysis, breath analysis, weight, body pH level, sclera color, pupil size, lip color analysis, skin color analysis, mini mental status exam, pain scale, electrocardiogram, and/or BMI. The system may take these inputs and make relevant determinations including a score, raw data, percentile, chart or graph, measurement of physical or mental response to a medication or supplement, possible medication or supplement overdose symptoms alert, and possible medication or supplement overdose signs alert.

Dispensing of prescriptions may be assessed and information provided. Assessments may include name, quantity, dose, administration, duration of usage, and refills. The system may provide a visual display of one or more of the following: substance name, substance remaining quantity, substance dosage, route of administration, allowed refills, and/or substance expiration date.

The present design may be used in various scenarios, including but not limited to use of the design for pets or animals as well as plants in addition to human personal care. In the pet scenario, the device may monitor a pet, such as a body temperature of a pet, using a module, and/or the location of a pet, such as using a collar with a GPS component or other position determining device. In the horticulture arrangement, for example, plant health may be monitored and plant care provided as appropriate. In one instance, a device may measure amount of water available to a tree, and if deficient, may notify a person or service to provide water to the plant, or may cause a sprinkler or watering apparatus to turn on automatically.

Thus the present design may include hardware and devices configured to facilitate personal care of a user. Personal care and other functionality may be provided in, for example, the areas of health, fitness, wellness, fashion, cosmetics, and/or pharmaceuticals. The system may include a device configured to receive personal health related modules, which are interchangeable, and may include a device having a mirror or reflective surface that acts as a computing device display. The device may include processing and data storage capabilities, and the user may freely exchange personal care modules as desired. The device may collect information and may provide the information to a remote device arrangement, including but not limited to the interne "cloud" and may process the information received. As an example, information regarding a desired weight goal may be provided, and health recommendations may be transmitted from the remote device arrangement to the device and the user. A handheld unit configured to receive information and possibly process the information may be provided so that the user may take the handheld unit with her to a remote location. Information for multiple devices may be maintained at the remote device arrangement, and differing levels of service may be provided.

Thus according to one embodiment, there is provided a device having a display/mirror and a plurality of connection ports each configured to receive a personal care module configured to facilitate the personal care of a user and a remote device arrangement. The device is configured to provide user personal care communications to and receive user personal care communications from the remote device arrangement, and wherein the device is configured for the user to freely substitute personal care modules.

According to a second embodiment, there is provided a method for facilitating personal care of a user. The method includes receiving, at a remote device arrangement, user personal care data transmitted by a user personal care computing device, determining at the remote device arrangement a user personal care recommendation specific for the user based on the user personal care data received, and transmitting the user personal care recommendation to the user personal care computing device.

According to another embodiment, there is provided a personal care device, comprising a computing device display that is a mirror, and a housing surrounding the computing device display that operates as the mirror, the housing comprising a plurality of connection ports configured to receive personal care modules configured to facilitate personal care of a user. The housing comprises one from a group consisting of a camera, a microphone, a speaker, a sensor, and a fingerprint reader.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. An apparatus, comprising:
a personal care combination display/mirror device comprising a surface operating as a reflective surface and a plurality of connection ports, each connection port configured to receive a hardware personal care module, each hardware personal care module configured to interact with the personal care combination display/mirror device to provide personal care functionality facilitating personal care of a user, wherein personal care comprises nutritional and pharmaceutical care; and
a remote central server device arrangement;
wherein the personal care combination display/mirror device is configured to transmit user personal care communications comprising user specific nutritional and pharmaceutical care communications personalized to the user to and receive user personal care communications personalized to the user from the remote central server device arrangement, and wherein the personal care combination display/mirror device is configured for the user to freely substitute selected and different hardware personal care modules in the plurality of connection ports, and further wherein at least one hardware personal care module interacts with the personal care combination display/mirror device to sense a current physical attribute of the user;
wherein a first hardware personal care module comprises a pharmaceutical personal care module and a second hardware personal care module comprises a nutritional personal care module, and wherein the pharmaceutical personal care module is used with the personal care combination display/mirror device to assess user pharmaceutical needs and provide pharmaceutical information and recommendations specifically for the user to the user, and the nutritional personal care module is used with the personal care combination display/mirror device to assess user nutritional status and provide nutritional information and recommendations specifically for the user to the user.

2. The apparatus of claim 1, wherein the personal care combination display/mirror device comprises a computing device display that functions as a reflective surface.

3. The apparatus of claim 1, wherein at least one connection port comprises a USB (Universal Serial Bus) connection port.

4. The apparatus of claim 1, wherein the personal care combination display/mirror device comprises a processor.

5. The apparatus of claim 4, wherein the personal care combination display/mirror device comprises a storage unit and communication components, wherein the communication components communicate with the remote central server device arrangement.

6. The apparatus of claim 1, wherein the personal care combination display/mirror device comprises at least one from a group consisting of a camera, a microphone, a speaker, a sensor, and a fingerprint reader.

7. The apparatus of claim 1, further comprising a handheld unit configured to interface with the personal care combination display/mirror device and collect user personal care data, wherein the handheld unit comprises at least one connection port.

8. The apparatus of claim 1, wherein the personal care combination display/mirror device is separately formed from a frame surrounding a display/mirror, and the frame includes the plurality of connection ports.

9. A method for facilitating personal care of a user, comprising:
receiving, at a remote central server device arrangement, user personal care data personalized to the user transmitted by a user personal care combination display/mirror computing device;

determining at the remote central server device arrangement a user personal care recommendation specifically for the user based on the user personal care data personalized to the user received; and transmitting the user personal care recommendation specifically for the user from the remote central server device to the user personal care combination display/mirror computing device, wherein the user personal care recommendation comprises at least one of a user specific nutritional care recommendation and a user specific pharmaceutical care recommendation;

wherein the user personal care combination display/mirror device comprises a plurality of connection ports, each connection port configured to receive a hardware personal care module, each hardware personal care module configured to interact with the personal care combination display/mirror device to provide personal care functionality facilitating personal care of a user;

wherein personal care comprises nutritional and pharmaceutical care;

and further wherein at least one hardware personal care module interacts with the personal care combination display/mirror device to sense a current physical attribute of the user;

wherein a first hardware personal care module comprises a pharmaceutical personal care module and a second hardware personal care module comprises a nutritional personal care module, and wherein the pharmaceutical personal care module is used with the personal care combination display/mirror device to assess user pharmaceutical needs and provide pharmaceutical information and recommendations specifically for the user to the user, and the nutritional personal care module is used with the personal care combination display/mirror device to assess user nutritional status and provide nutritional information and recommendations specifically for the user to the user.

10. The method of claim 9 wherein the remote central server device arrangement comprises a plurality of computing devices.

11. The method of claim 9, wherein the user personal care data received has been collected using a hardware personal care module connected to the user personal care combination display/mirror computing device.

12. The method of claim 9, wherein the user personal care data received has been collected using a handheld unit, wherein the method further comprises transmitting the user personal care data from the handheld unit to the user personal care combination display/mirror computing device.

13. A personal care combination display/mirror device, comprising:

a computing device display that operates as a mirror; and a housing surrounding the computing device display that operates as the mirror, the housing comprising a plurality of connection ports configured to receive hardware personal care modules, each hardware personal care module configured to interact with the computing device display that operates as a mirror to provide personal care functionality facilitating personal care of a user, wherein personal care comprises;

wherein the housing comprises at least one from a group consisting of a camera, a microphone, a speaker, a sensor, and a fingerprint reader, and further wherein the personal care device is configured to employ at least one hardware personal care module to sense a current physical attribute of the user, determine a personal care recommendation specific to the user, and display the personal care recommendation to the user using the computing device display, wherein the personal care recommendation provides at least one of a pharmaceutical personal care recommendation and a nutritional personal care recommendation;

wherein a first hardware personal care module comprises a pharmaceutical personal care module and a second hardware personal care module comprises a nutritional personal care module, and wherein the pharmaceutical personal care module is used with the personal care combination display/mirror device to assess user pharmaceutical needs and provide pharmaceutical information and recommendations specifically for the user to the user, and the nutritional personal care module is used with the personal care combination display/mirror device to assess user nutritional status and provide nutritional information and recommendations specifically for the user to the user.

14. The personal care combination display/mirror device of claim 13, further comprising a processor, a data storage device, and a communication arrangement.

15. The personal care combination display/mirror device of claim 14, wherein the processor collects user personal care data received from a handheld unit.

16. The personal care combination display/mirror device of claim 13, wherein at least one connection port comprises a USB (Universal Serial Bus) connection port.

17. The apparatus of claim 1, wherein the personal care combination display/mirror device comprises:
a two dimensional display/mirror;
a three dimensional display/mirror; or
a holographic display mirror.

* * * * *